United States Patent
Yamaguchi et al.

(10) Patent No.: US 9,596,982 B2
(45) Date of Patent: Mar. 21, 2017

(54) ENDOSCOPE SYSTEM AND COMPOSITE IMAGE GENERATION METHOD

(71) Applicant: FUJIFILM Corporation, Tokyo (JP)

(72) Inventors: Hiroshi Yamaguchi, Ashigarakami-gun (JP); Satoshi Ozawa, Ashigarakami-gun (JP); Takayuki Iida, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 457 days.

(21) Appl. No.: 14/250,120

(22) Filed: Apr. 10, 2014

(65) Prior Publication Data

US 2014/0221744 A1 Aug. 7, 2014

Related U.S. Application Data

(63) Continuation of application No. PCT/JP2012/076298, filed on Oct. 11, 2012.

(30) Foreign Application Priority Data

Oct. 12, 2011 (JP) ................................ 2011-225140
Sep. 4, 2012 (JP) ................................ 2012-193907

(51) Int. Cl.
*A61B 1/04* (2006.01)
*A61B 1/06* (2006.01)
(Continued)

(52) U.S. Cl.
CPC ........ *A61B 1/0638* (2013.01); *A61B 1/00009* (2013.01); *A61B 1/05* (2013.01);
(Continued)

(58) Field of Classification Search
None
See application file for complete search history.

(56) References Cited

U.S. PATENT DOCUMENTS

2007/0088192 A1* 4/2007 Takeuchi ........... A61B 1/00009
600/101
2011/0071352 A1 3/2011 Ozawa et al.
(Continued)

FOREIGN PATENT DOCUMENTS

EP 1 568 307 A1 8/2005
EP 2 328 339 A2 6/2011
(Continued)

OTHER PUBLICATIONS

International Search Report issued in PCT/JP2012/076298, dated Nov. 20, 2012.
(Continued)

*Primary Examiner* — John P Leubecker
(74) *Attorney, Agent, or Firm* — Birch, Stewart, Kolasch & Birch, LLP

(57) ABSTRACT

A blue signal B, a green signal G, and a red signal R are obtained by imagining a subject illuminated with white light W using a color CCD 44. Based on these signals B, G, and R, a normal light image in which a wavelength component of a visible light region is included is generated. Based on the signals B, G, and R, a brightness signal I ((B+G+R)/3) showing the average brightness of the subject is generated. A pixel region exceeding the fixed threshold value Th1 of the brightness signal I is extracted as a superficial microstructure P, such as a pit pattern. A microstructure enhancement image 72 is generated by combining the normal light image with a superficial microstructure image 70 obtained by extracting the superficial microstructure P. The generated microstructure and blood vessel enhancement image 72 is displayed on a monitor 14.

19 Claims, 24 Drawing Sheets

(51) Int. Cl.
 *A61B 1/00* (2006.01)
 *A61B 1/05* (2006.01)
 *G06T 5/50* (2006.01)
 *G06T 7/00* (2017.01)
(52) U.S. Cl.
 CPC .............. *A61B 1/0653* (2013.01); *G06T 5/50* (2013.01); *G06T 7/0081* (2013.01); *G06T 2207/10024* (2013.01); *G06T 2207/10068* (2013.01); *G06T 2207/10152* (2013.01); *G06T 2207/20148* (2013.01); *G06T 2207/20221* (2013.01)

(56) References Cited

U.S. PATENT DOCUMENTS

| | | | | |
|---|---|---|---|---|
| 2011/0071353 | A1* | 3/2011 | Ozawa | A61B 1/0638 600/109 |
| 2011/0077462 | A1* | 3/2011 | Saitou | A61B 1/0638 600/109 |
| 2011/0112362 | A1* | 5/2011 | Minetoma | A61B 1/05 600/109 |
| 2011/0199500 | A1* | 8/2011 | Shimizu | A61B 1/00009 348/222.1 |
| 2011/0237882 | A1* | 9/2011 | Saito | A61B 1/00009 600/109 |
| 2011/0237895 | A1* | 9/2011 | Yoshida | A61B 1/00009 600/180 |
| 2011/0237915 | A1* | 9/2011 | Yamaguchi | A61B 1/00009 600/339 |
| 2012/0120217 | A1* | 5/2012 | Sasaki | A61B 1/00006 348/65 |
| 2012/0190922 | A1* | 7/2012 | Kaku | A61B 1/00009 600/109 |
| 2012/0197076 | A1* | 8/2012 | Minetoma | A61B 1/00009 600/109 |
| 2012/0220840 | A1* | 8/2012 | Morita | A61B 1/00009 600/317 |
| 2012/0302847 | A1* | 11/2012 | Ozawa | A61B 1/00009 600/339 |
| 2012/0327186 | A1* | 12/2012 | Kitamura | A61B 1/00009 348/45 |
| 2012/0327205 | A1* | 12/2012 | Takahashi | A61B 1/04 348/65 |
| 2013/0044126 | A1* | 2/2013 | Yamada | H04N 7/183 345/629 |

FOREIGN PATENT DOCUMENTS

| | | |
|---|---|---|
| JP | 8-252218 A | 10/1996 |
| JP | 2001-170009 A | 6/2001 |
| JP | 2010-94153 A | 4/2010 |

OTHER PUBLICATIONS

Written Opinion of the International Searching Authority issued in PCT/JP2012/076298, dated Nov. 20, 2012.
Extended European Search Report, dated Jul. 29, 2015, for European Application No. 12839233.9.
Japanese Notice of Reasons for Rejection and English translation thereof, dated Jul. 8, 2015, for Japanese Application No. 2012-193907.

* cited by examiner

US 9,596,982 B2

ENDOSCOPE SYSTEM AND COMPOSITE IMAGE GENERATION METHOD

CROSS REFERENCE TO RELATED APPLICATIONS

This application is a Continuation of PCT International Application No. PCT/JP2012/076298 filed on Oct. 11, 2012, which claims priority under 35 U.S.C. §119(a) to Patent Application No. 2011-225140 filed in Japan on Oct. 12, 2011 and Patent Application No. 2012-193907 filed in Japan on Sep. 4, 2012, all of which are hereby expressly incorporated by reference into the present application.

BACKGROUND OF THE INVENTION

1. Field of the Invention

The present invention relates to an endoscope system capable of clearly observing a blood vessel pattern such as a superficial microvessel, a microstructure such as a pit pattern, or an irregular pattern such as hypertrophy, and an image generation method.

2. Description of the Related Art

In recent medical treatment, diagnosis or the like using an endoscope apparatus has been widely performed. In this endoscopic diagnosis, not only normal light observation, in which white light of broadband light is used as illumination light within the subject, but also special light observation, in which a lesion, such as cancer, is made clearer than other parts or the position or the size of the lesion is easily intuitively grasped by using the special light having a specific wavelength as illumination light, is performed.

For example, in JP2001-170009A, using the fact that the degree of penetration in the depth direction of the body tissue and the absorption characteristics of hemoglobin in the blood have a wavelength dependency, a microstructure such as a pit pattern or a microvessel formed in a body tissue surface layer is made clear with blue narrow-band light having a short wavelength, and a thick blood vessel located in a medium-deep layer of the body tissue is made clear with green narrow-band light having a longer wavelength than that of the blue narrow-band light. Blood vessels or superficial microstructures of the surface to medium-deep layers are important clues at the time of differential diagnosis of cancer or degree-of-penetration diagnosis. Therefore, it is possible to greatly improve the accuracy of differentiation and the like by making the blood vessels or the superficial microstructures of the surface to medium-deep layers clear using blue narrow-band light or green narrow-band light.

In addition, in JP1996-252218A (JP-H08-252218A), a boundary between a lesion part and a normal part is made clear by using the characteristic that the amount of auto-fluorescence emitted from the lesion part, which is thickened due to the lesion such as cancer, is less than the amount of auto-fluorescence from the normal part, which is not thickened, when irradiating the body tissue with excitation light for exciting the auto-fluorescence. By making the boundary between the lesion part and the normal part clear as described above, it becomes easy to grasp the position or the size of the lesion part when performing observation from a distant-view state as at the time of screening.

SUMMARY OF THE INVENTION

In recent years, there are various kinds of cancer differentiation methods or methods for degree-of-penetration diagnosis. Accordingly, there is not only a case where cancer diagnosis is performed from both a blood vessel pattern, such as a superficial microvessel or a medium-deep layer blood vessel, and an irregular pattern, such as a superficial microstructure or hypertrophy, but also a case where diagnosis is performed by focusing only on the irregular pattern. For this reason, an endoscope system capable of not only making both a blood vessel pattern and an irregular pattern clear but also making only the irregular pattern clear has been requested.

In this regard, according to the method disclosed in JP2001-170009A, both a blood vessel pattern and an irregular pattern can be made clear. However, since a narrow-band wavelength is used in order to make the blood vessel pattern and the irregular pattern clear, the brightness of the entire subject is reduced. Therefore, since an image obtained in a situation where the distance from an observation region is great as in a distant-view state becomes a dark image with the reduced amount of light, the image is not suitable for diagnosis. In addition, according to the method disclosed in JP1996-252218A (JP-H08-252218A), it is possible to grasp the position or the range of the hypertrophy that is one of irregular patterns, but it is difficult to accurately grasp the shape or the size of the irregular pattern since an obtained image is a complete pseudo-color image.

It is an object of the present invention to provide an endoscope system and an image generation method capable of obtaining a bright image in which a blood vessel pattern or an irregular pattern is clear.

In order to achieve the above-described object, an endoscope system of the present invention includes: an image signal acquisition unit for acquiring an image signal by imaging a subject; a normal light image generation unit that generates a normal light image, in which a wavelength component of a visible light region is included, based on the image signal; an irregularity image generation unit that generates an irregularity image by extracting only information of irregularities on the subject from the image signal; and first composite image generation unit that generates a first composite image by combining the normal light image with the irregularity image.

Preferably, the irregularity image generation unit includes a microstructure image generation section that generates a microstructure image as the irregularity image by extracting only a microstructure of a body tissue surface layer from the image signal, and the first composite image generation unit includes a normal light image and microstructure image combination section that generates a first composite image by combining the normal light image with the microstructure image. Preferably, the irregularity image generation unit includes a hypertrophy image generation section that generates a hypertrophy image as the irregularity image by extracting from the image signal only hypertrophy having a thickness from a body tissue surface layer to medium-deep layer, and the first composite image generation unit includes a normal light image and hypertrophy image combination section that generates a first composite image by combining the normal light image with the hypertrophy image.

In the present invention, it is preferable to further include: blood vessel extraction image generation unit that generates a blood vessel extraction image by extracting a blood vessel located at the specific depth in the subject based on the image signal; and second composite image generation unit that generates a second composite image by combining the normal light image, the blood vessel extraction image, and the irregularity image. Preferably, the image signal is configured to include image signals of a plurality of colors including at least a blue signal, which has a blue light component having a degree of penetration to a surface layer of body tissue of the subject, and a green signal, which has a green light component having a degree of penetration to a medium-deep layer of the body tissue, and the blood vessel extraction image generation unit extracts the blood vessel at the specific depth based on a ratio of the signal and the green signal of the image signals of the plurality of colors. Preferably, frequency filtering of a frequency corresponding to a depth of a blood vessel is performed on the blood vessel extraction image.

Preferably, imaging of the subject is performed by a color imaging device having pixels of a plurality of colors in which respective color separation filters are provided. Preferably, the endoscope system of the present invention further includes illumination unit that sequentially irradiates the subject with light beams of a plurality of colors, and imaging of the subject is performed by a monochrome imaging device whenever sequential irradiation is performed by the illumination unit. Preferably, the endoscope system of the present invention further includes display unit that displays the irregularity image.

An image generation method of the present invention includes: acquiring an image signal by imaging a subject with an imaging device; generating a normal light image, in which a wavelength component of a visible light region is included, based on the image signal using a normal light image generation unit; generating an irregularity image by extracting only information of irregularities on the subject from the image signal using irregularity image generation unit; and generating a first composite image by combining the normal light image with the irregularity image using first composite image generation unit.

According to the present invention, the first composite image obtained by the first composite image generation unit is an image obtained by combining the normal light image with the irregularity image obtained by extracting only the information of the irregularities on the subject. Therefore, only an irregular pattern on body tissue, such as a superficial microstructure or hypertrophy, is made clear in a state where the entire brightness is ensured. In addition, the second composite image obtained by the second composite image generation unit is an image obtained by combining the normal light image with the irregularity image and the blood vessel extraction image obtained by extracting the blood vessel at the specific depth. Therefore, an irregular pattern and a blood vessel pattern, such as a superficial microvessel, are made clear in a state where the entire brightness is ensured.

DESCRIPTION OF THE PREFERRED EMBODIMENTS

Figure 1:
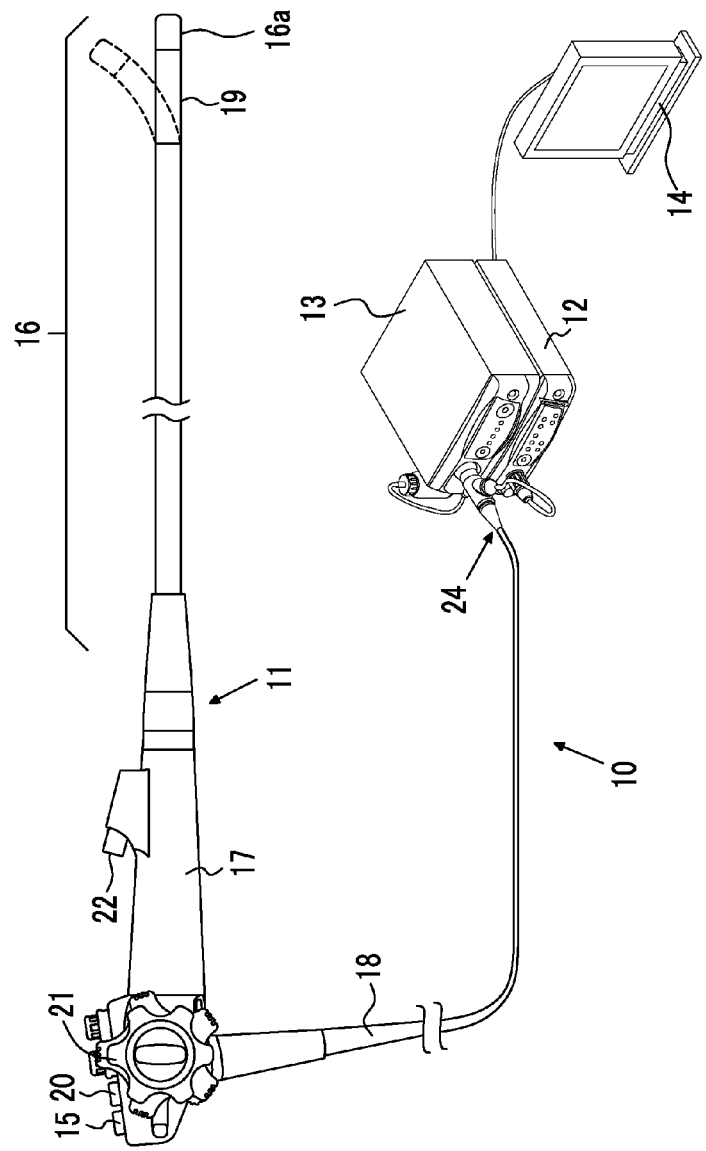
FIG. 1 is a diagram showing an endoscope system of a first embodiment.
Figure 2:
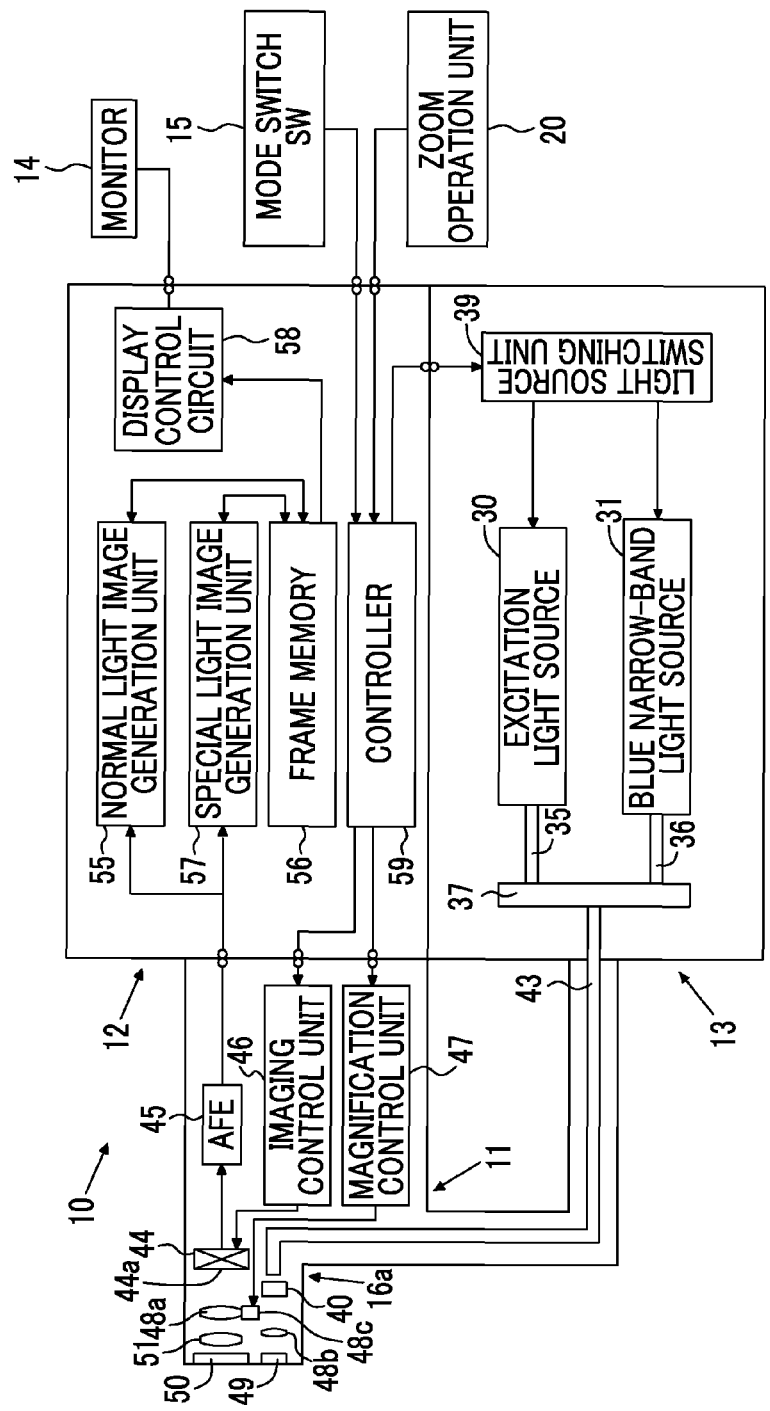
FIG. 2 is a diagram showing the internal configuration of the endoscope system of the first embodiment.

As shown in FIGS. 1 and 2, en endoscope system 10 of the first embodiment includes: an electronic endoscope 11 (a form of image signal acquisition unit) that images the inside of a subject, a processor device 12 that performs various kinds of image processing on the image captured by the electronic endoscope 11; a light source device 13 that supplies light for illuminating the subject to the electronic endoscope 11; and a monitor 14 that displays an image after various kinds of image processing are performed by the processor device 12.

The electronic endoscope 11 includes a flexible insertion unit 16 that is inserted into the subject, an operating unit 17 provided at the proximal end of the insertion unit 16, and a universal code 18 that makes a connection between the operating unit 17 and the processor device 12 and the light source device 13. A curved portion 19 obtained by connecting a plurality of curved pieces is formed at the distal end of the insertion unit 16. The curved portion 19 is curved in the horizontal and vertical directions by operating an angle knob 21 of the operating unit 17. A distal portion 16a including an optical system for imaging the body cavity and the like is provided at the distal end of the curved portion 19. The distal portion 16a is directed in a desired direction within the subject by the bending operation of the curved portion 19.

In addition, a mode switch SW 15 for switching to various modes is provided in the operating unit 17. The various modes include a total of five modes of a normal observation mode in which a normal light image obtained by imaging a subject illuminated with white light is displayed on the monitor 14, a superficial microstructure observation mode in which a superficial microstructure enhancement image emphasizing the microstructure formed on the surface layer of body tissue is displayed on the monitor 14, a hypertrophy observation mode in which a hypertrophy enhancement image that emphasizes a hypertrophy having a thickness from the surface layer to the medium-deep layer in body tissue is displayed on the monitor 14, a microstructure and blood vessel observation mode in which a microstructure and blood vessel enhancement image emphasizing the superficial microstructure and the blood vessel located at a specific depth is displayed on the monitor 14, and a hypertrophy and blood vessel observation mode in which a hypertrophy and blood vessel enhancement image emphasizing hypertrophy and the blood vessel located at a specific depth is displayed on the monitor 14.

A connector 24 is attached to the universal code 18 on the side of the processor device 12 and the light source device 13. The connector 24 is a composite connector including a communication connector and a light source connector, and the electronic endoscope 11 is detachably connected to the processor device 12 and the light source device 13 through the connector 24.

The light source device 13 includes: an excitation light source 30 that emits excitation light EL having a specific wavelength; a blue narrow-band light source 31 that emits blue narrow-band light BN that is narrowed to a specific wavelength in the blue band; an optical fiber for excitation light 35 on which the excitation light EL from the excitation light source 30 is incident; and optical fiber for blue narrow-band light 36 on which the blue narrow-band light BN from the blue narrow-band light source 31 is incident; a coupler 37 that optically couples the optical fibers 35 and 36 with a light guide 43 in the electronic endoscope; and a light source switching unit 39 for ON/OFF switching of the excitation light source 30 and the blue narrow-band light source 31.

Figure 3:
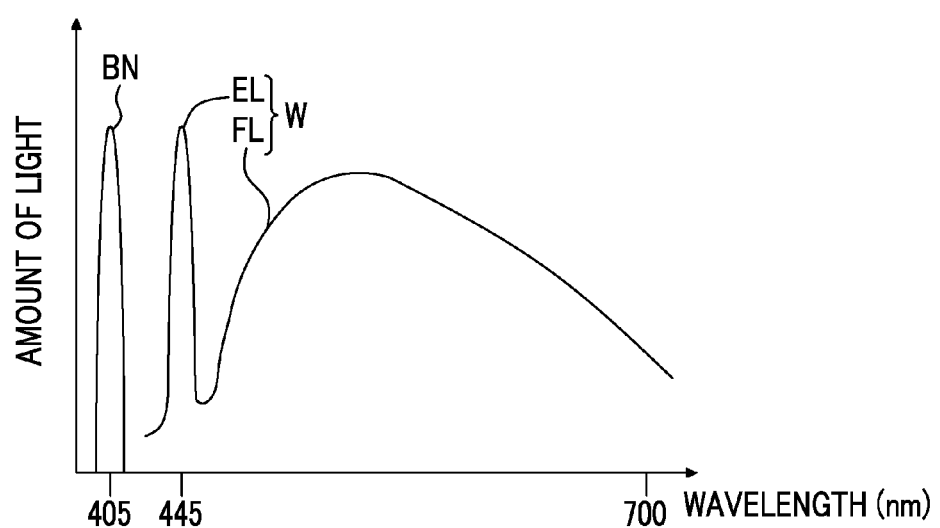
FIG. 3 is a graph showing the emission spectrum of white light W that is excited and emitted by excitation light.

The excitation light source 30 is a semiconductor light source, such as a laser diode, and emits the excitation light EL having a center wavelength of 445 nm as shown in FIG. 3. The excitation light EL is irradiated to a phosphor 40, which is provided in the distal portion 16a of the electronic endoscope 11, through the optical fiber for excitation light 35, the coupler 37, and the light guide 43. The phosphor 40 is configured to include a plurality of kinds of fluorescent materials (for example, a YAG-based fluorescent material or a fluorescent material, such as BAM ($BaMgAl_{10}O_{17}$) that absorb a part of the excitation light EL and excite and emit fluorescence FL of green to red. As shown in FIG. 3, the fluorescence FL excited and emitted by the phosphor 40 is combined with the excitation light EL that is transmitted through the phosphor 40 without being absorbed by the phosphor 40, thereby generating white light W.

The blue narrow-band light source 31 is a semiconductor light source, such as a laser diode, and emit the blue narrow-band light BN having a center wavelength of 405 nm as shown in FIG. 3. Since the blue narrow-band light BN has a degree of penetration to the surface layer of body tissue, the blue narrow-band light BN is used in order to brightly illuminate the superficial microstructure of body tissue, such as a pit pattern.

The light source switching unit 39 is connected to a controller 59 in the processor device, and switches the excitation light source 30 and the blue narrow-band light source 31 ON (lighting) and OFF (lighting off) according to the mode that is set. When the normal observation mode, the hypertrophy observation mode, and the hypertrophy and blood vessel observation mode are set, the excitation light source 30 is always ON while the blue narrow-band light source 31 is always OFF. Accordingly, only the white light W is always irradiated to the subject. In contrast, when the superficial microstructure observation mode or the microstructure and blood vessel observation mode is set, the excitation light source 30 is always ON while the blue narrow-band light source 31 is switched ON and OFF in every other frame. Accordingly, irradiation of only the white light W and simultaneous irradiation of the white light W and the blue narrow-band light BN are alternately repeated every other frame.

The electronic endoscope 11 includes the light guide 43, a CCD 44, an analog processing circuit 45 (AFE: Analog Front End), an imaging control unit 46, and a magnification control unit 47. The light guide 43 is a large-diameter optical fiber, a bundle fiber, or the like, and the incidence end is inserted in the coupler 37 of the light source device and the exit end is directed to the phosphor 40. Light guided by the light guide 43 is irradiated to the subject through the phosphor 40, an irradiation lens 48b, and an illumination window 49. An observation window 50 receives returned light from the subject. The received light is incident on the CCD 44 through a condensing lens 51 and a zoom lens 48a.

Figure 4A:
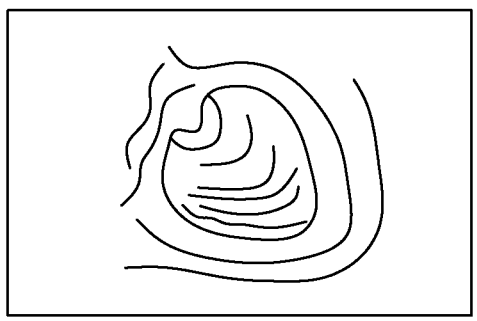
FIG. 4A is a diagram showing a non-enlarged image captured when the zoom lens is located at wide-angle position.
Figure 4B:
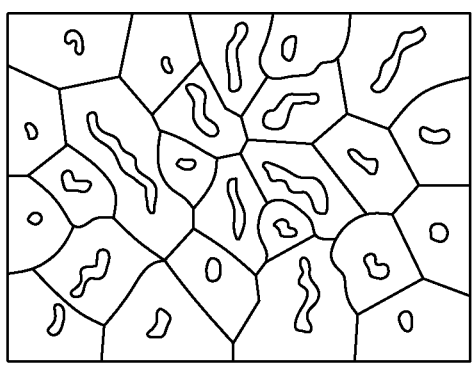
FIG. 4B is a diagram showing an enlarged image captured when the zoom lens is located at a telephoto position.

An actuator 48c to move the zoom lens 48a in the optical axis direction is attached to the zoom lens 48a. The driving of the actuator 48c is controlled by the magnification control unit 47 connected to the controller 59. The magnification control unit 47 controls the actuator 48c so that the zoom lens 48a moves to a position corresponding to the magnification set by a zoom operation unit 20. When it is necessary to observe the overall condition in the subject, for example, at the time of screening, the zoom lens 48a is set to a wide-angle position so that a non-enlarged image shown in FIG. 4A is displayed on the monitor 14. On the other hand, when it is necessary to observe the detailed structure of a part to be observed, for example, at the time of differential diagnosis of cancer, the zoom lens 48a is set to a telephoto position so that an enlarged image shown in FIG. 4B is displayed on the monitor 14.

In the normal observation mode, the hypertrophy observation mode, and the hypertrophy and blood vessel observation mode, the overall condition in the subject is observed in many cases. Therefore, the zoom lens 48a is set to the wide-angle position in many cases. On the other hand, in the superficial microstructure observation mode and the microstructure and blood vessel observation mode, an object to be observed is enlarged and observed in many cases. Therefore, the zoom lens 48a is set to the telephoto position in many cases.

Figure 5:
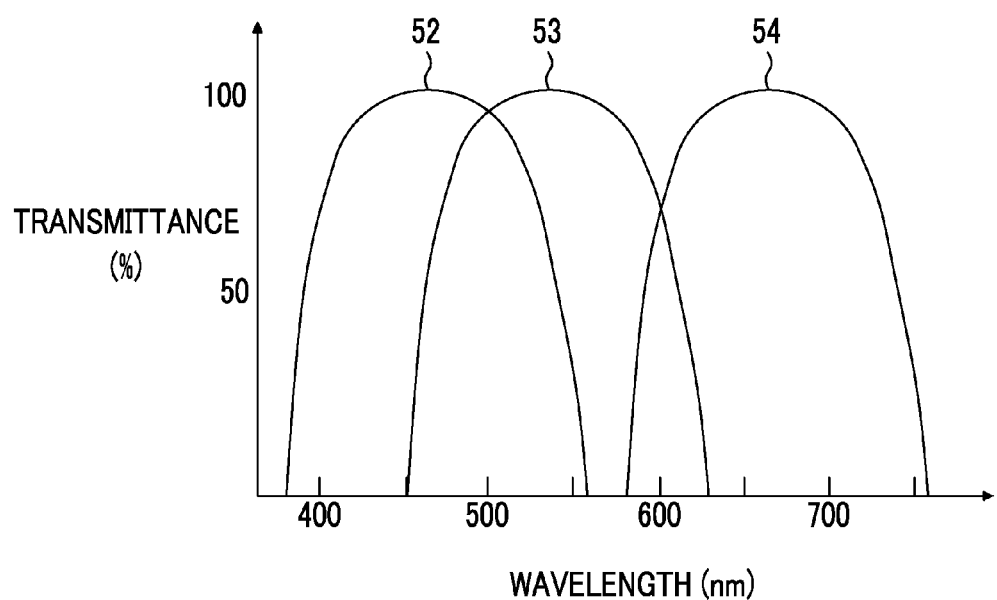
FIG. 5 is a graph showing the spectral transmittances of color filters of R, G, and B colors.

The CCD 44 has an imaging surface 44a on which light from the condensing lens 51 is incident, and performs photoelectric conversion of the light received by the imaging surface 44a and accumulates the signal charges. The accumulated signal charges are read as an imaging signal, and the imaging signal is transmitted to the AFE 45. The CCD 44 is a color CCD, and pixels of three colors of a B pixel in which a color filter of B color is provided, a G pixel in which a color filter of G color is provided, and an R pixel in which a color filter of R color is provided are arrayed on the imaging surface 44a. These color filters of B, G, and R colors have spectral transmittances indicated by curves 52, 53, and 54 shown in FIG. 5.

The AFE 45 is configured to include a correlated double sampling circuit (CDS), an automatic gain control circuit (ARC), and an analog/digital converter (A/D) (all not shown). The CDS performs correlated double sampling processing on an imaging signal from the CCD 44 to remove noise caused by the driving of CCD 44. The AGC amplifies an imaging signal from which noise has been removed by the CDS. The A/D converts an imaging signal amplified by the AGC into a digital imaging signal of a predetermined number of bits, and inputs the digital imagining signal to the processor device 12.

The imaging control unit 46 is connected to the controller 59 in the processor device 12, and transmits a driving signal to the CCD 44 when there is an instruction from the controller 59. The CCD 44 outputs an imaging signal to the AFE 45 at a predetermined frame rate based on the driving signal from the imaging control unit 46.

Figure 6A:
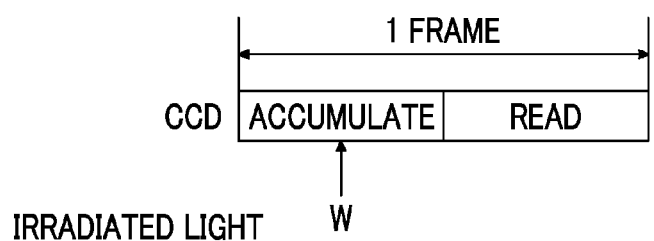
FIG. 6A is a diagram for explaining the imaging control of a CCD in a normal observation mode, a hypertrophy observation mode, and a hypertrophy and blood vessel observation mode in the first embodiment.

In the normal observation mode, the hypertrophy observation mode, and the hypertrophy and blood vessel observation mode, as shown in FIG. 6A, a step of performing photoelectric conversion of image light of the white light W and accumulating the signal charges and a step of reading the accumulated signal charges are performed within one frame period. This imaging control is repeatedly performed while the normal observation mode, the hypertrophy observation mode, and the hypertrophy and blood vessel observation mode are set. In each read step, a blue signal B, a green signal G, and a red signal R are respectively output from the B, G, and R pixels of the CCD 44.

Figure 6B:
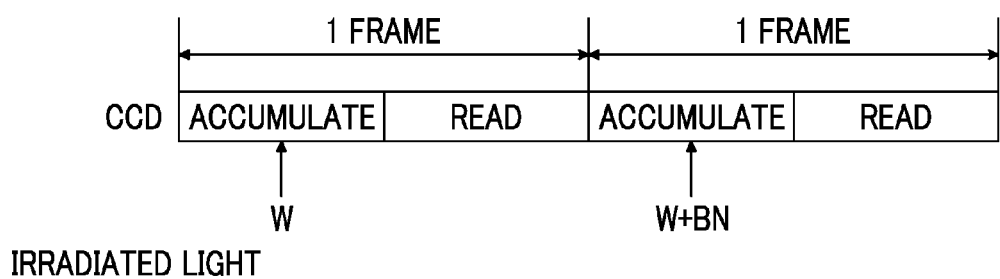
FIG. 6B is a diagram for explaining the imaging control of the CCD in a superficial microstructure observation mode and a microstructure and blood vessel observation mode in the first embodiment.

When the superficial microstructure observation mode or the microstructure and blood vessel observation mode is set, as shown in FIG. 6B, a step of performing photoelectric conversion of image light of the white light W and accumulating the signal charges and a step of reading the accumulated signal charges are performed within one frame period. Then, a step of performing photoelectric conversion of image light of the white light W and the blue narrow-band light BN and accumulating the signal charges and a step of reading the accumulated signal charges are performed within one frame period. This imaging control of two frames is repeatedly performed while the surface layer observation mode is set. In each read step, a blue signal B1, a green signal G1, and a red signal R1 are respectively output from the B, G, and R pixels of the CCD 44 in the first frame, and a blue signal B2, a green signal G2, and a red signal R2 are respectively output from the B, G, and R pixels in the next, second frame.

As shown in FIG. 2, the processor device 12 includes a normal light image generation unit 55 (a form of normal light image generation unit), a frame memory 56, a special light image generation unit 57 (a form of irregularity image generation unit), and a display control circuit 58. The controller 59 controls each of the units. The normal light image generation unit 55 generates a normal light image from a signal obtained by imaging the image light of the white light W with the electronic endoscope 11. That is, in the normal observation mode, the hypertrophy observation mode, and the hypertrophy and blood vessel observation mode, a normal light image is generated from the blue signal B, the green signal G, and the red signal R. In the superficial microstructure observation mode or the microstructure and blood vessel observation mode, a normal light image is generated from the blue signal B1, the green signal G1, and the red signal R1. The generated normal light image is temporarily stored in the frame memory 56.

Figure 7:
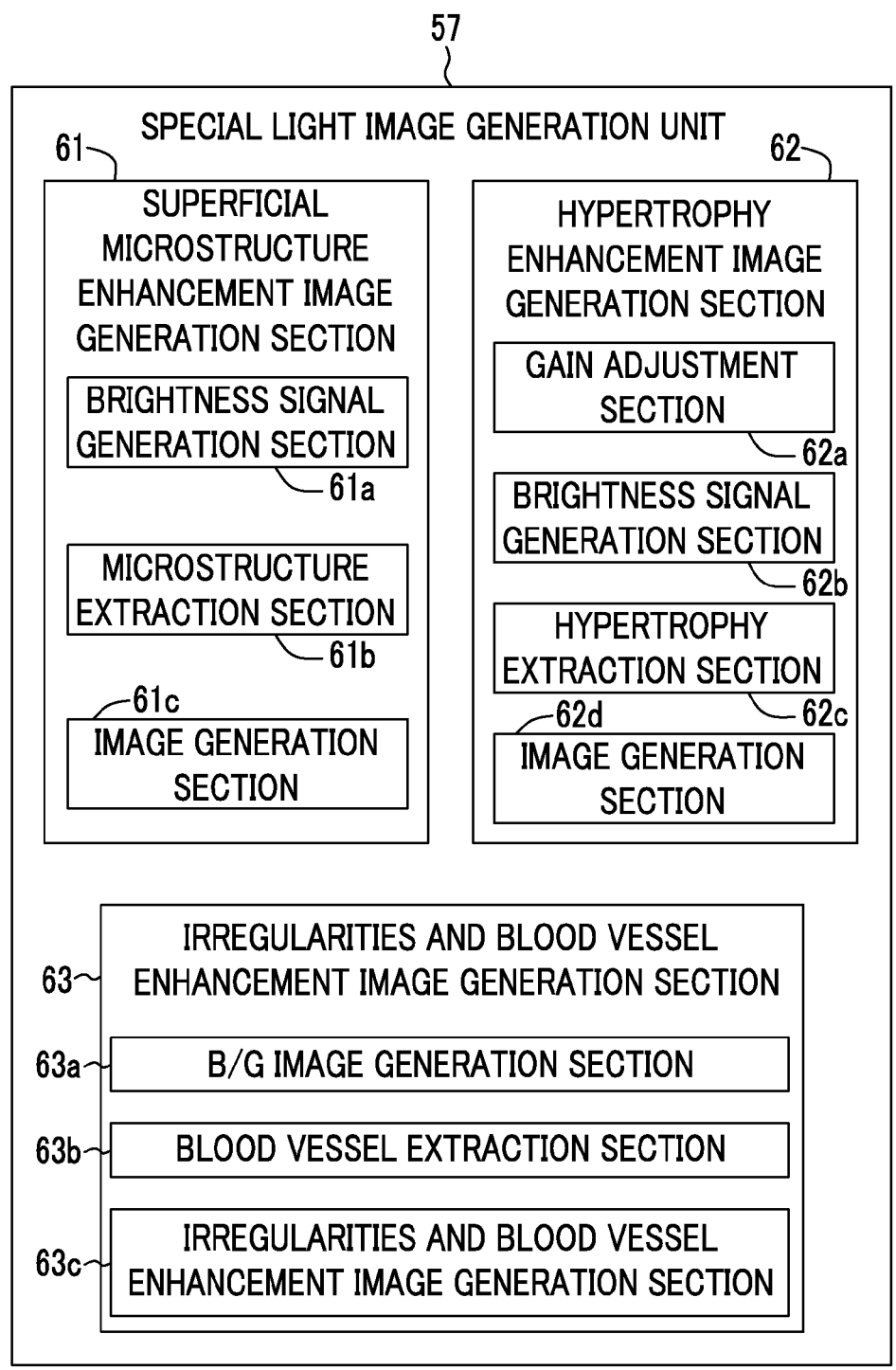
FIG. 7 is a diagram showing the internal configuration of a special light image generation unit.

As shown in FIG. 7, the special light image generation unit 57 includes a superficial microstructure enhancement image generation section 61, a hypertrophy enhancement image generation section 62, and an irregularities and blood vessel enhancement image generation section 63. The superficial microstructure enhancement image generation section 61 includes a brightness signal generation section 61a that generates a brightness signal I indicating the average brightness of the subject, a microstructure extraction section 61b (microstructure image generation section) that extracts a superficial microstructure image from the brightness signal I, and an image generation section 61c (normal light image and microstructure image combination section that is first composite image generation unit) that generates a superficial microstructure enhancement image by combining the normal light image with the superficial microstructure image extracted by the microstructure extraction section 61b.

Figure 8A:
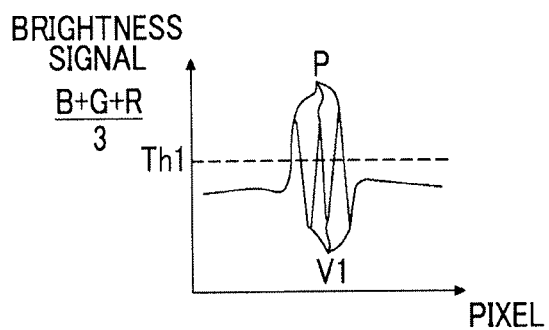
FIGS. 8A-8C are diagrams for explaining a method of generating a superficial microstructure image.
Figure 8B:
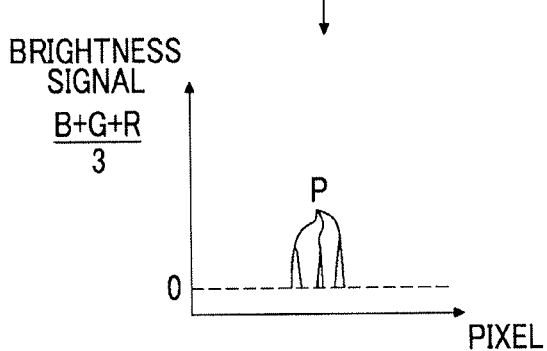

The brightness signal generation section 61a generates the brightness signal I (=(B2+G2+R2)/3) by dividing the total value (B2+G2+R2) of the signal values of the signals B2, G2, and R2 of the second frame, which are obtained in the superficial microstructure observation mode or the microstructure and blood vessel observation mode, by 3. Since the brightness signal I is obtained by averaging the signal values of the respective colors, the brightness signal I indicates the average brightness of the subject. As shown in FIG. 8A, the microstructure extraction section 61b extracts a pixel region, which exceeds a fixed high-brightness threshold value Th1 of the brightness signal I, as a superficial microstructure P. As shown in FIG. 8B, in a superficial microstructure image in which the superficial microstructure P is extracted, the pixel value of the brightness signal I is used as it is for a pixel region exceeding the high-brightness threshold value Th1, while the pixel value is set to "0" for a pixel region equal to or less than the high-brightness threshold value Th1.

The reason why the pixel region exceeding the high-brightness threshold value Th1 is set as the superficial microstructure P as described above is as follows. The superficial microstructure is formed of a pit pattern in which micropores formed on the body tissue surface layer gather, for example. Accordingly, when white light or the blue narrow-band light BN is incident on the micropores of the pit pattern, a multiple scattering phenomenon occurs so that the micropores shine brightly. Therefore, a bright region exceeding the high-brightness threshold value Th1 is set as a superficial microstructure. In addition, the superficial microvessel V1 is present between gland ducts in many cases. Since the superficial microvessel shows the strong absorption characteristics for the blue component or the blue narrow-band light BN of white light, the superficial microvessel is displayed darkly on the image. Accordingly, since the brightness of the superficial microvessel V1 is almost less than the high-brightness threshold value Th, superficial microvessels are hardly present (hardly included) in the superficial microstructure image.

Figure 8C:
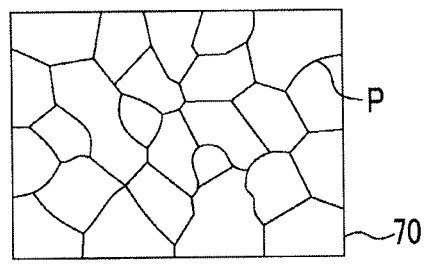

Then, high-frequency filtering processing is performed on the superficial microstructure image. The brightness value of a part corresponding to the superficial microstructure P changes greatly compared with other parts. Therefore, as shown in FIG. 8C, a superficial microstructure image 70 in which only the superficial microstructure P is sharply extracted is obtained by performing high-frequency filtering.

Figure 9:
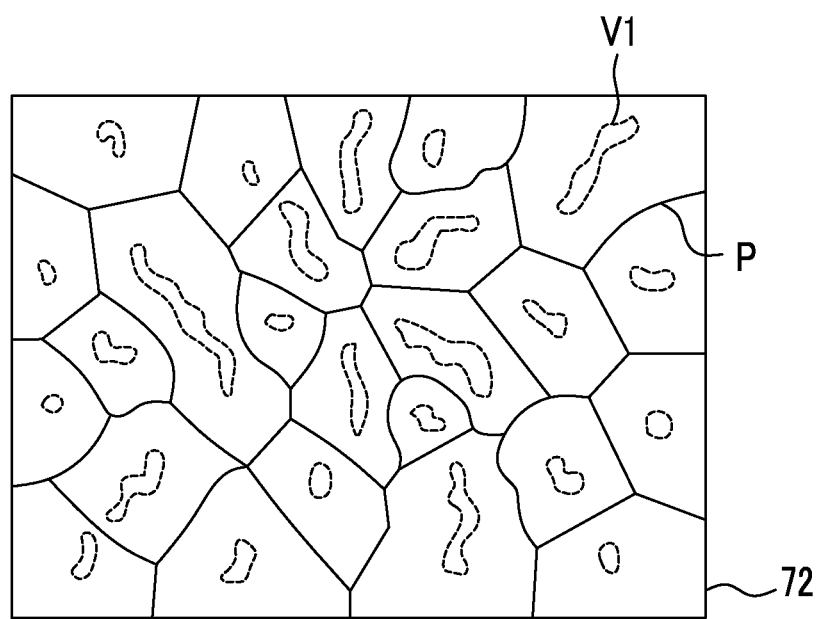
FIG. 9 is a diagram showing a superficial microstructure enhancement image.

The image generation section 61c generates a superficial microstructure enhancement image 72 shown in FIG. 9 by combining the normal light image with the superficial microstructure image 70 obtained by the microstructure extraction section 61b. The generated superficial microstructure enhancement image 72 is displayed on the monitor 14 by the display control circuit 58. Since the superficial microstructure enhancement 72 is based on the bright normal image, it is possible to perform diagnosis while securing the visibility. In the superficial microstructure enhancement image 72, only the superficial microstructure P of the body tissue of the surface layer other than a superficial microvessel V1 is clear. Accordingly, the superficial microstructure enhancement image 72 is an image that is suitable when performing cancer diagnosis by focusing on only the superficial microstructure P.

As shown in FIG. 7, the hypertrophy enhancement image generation section 62 includes: a gain adjustment section 62a that adjusts the gain of the signal B, G, and R in order to increase a signal including the information of a hypertrophy portion; a brightness signal generation section 62b that generates the brightness signal I indicating the average brightness of the subject from the signals B, G, and R after gain adjustment; a hypertrophy extraction section 62c (hypertrophy image generation section) that extracts a hypertrophy image from the brightness signal I; and an image generation section 62d (normal light image and hypertrophy image combination section that is first composite image generation unit) that generates a hypertrophy enhancement image by combining the normal light image with the hypertrophy image extracted by the hypertrophy extraction section.

The gain adjustment section 62a multiplies a pixel value by the gain of 1 or less for the signal B of the signals B, G, and R obtained in the hypertrophy observation mode or the hypertrophy and blood vessel observation mode, and multiplies a pixel value by the gain of 1 or more for the signals G and R. Since the hypertrophy has a thickness from the surface layer to the medium-deep layer, a lot of information regarding the hypertrophy is included not in the reflected light of light having a short wavelength less than 500 nm but in the reflected light of light having a long wavelength exceeding 500 nm. Therefore, the information regarding the hypertrophy can be made to be noticeable by reducing the pixel value of the signal B including a lot of information of the reflected light of light having a wavelength less than 500 nm and increasing the pixel values of the signals G and R including a lot of information of the reflected light of light having a wavelength exceeding 500 nm.

Figure 10A:
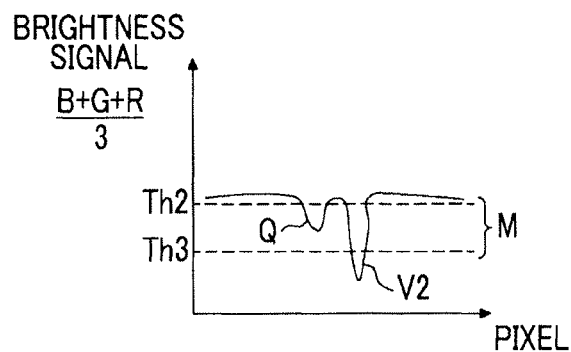
FIGS. 10A-10C are diagrams for explaining a method of generating a hypertrophy image.
Figure 10B:
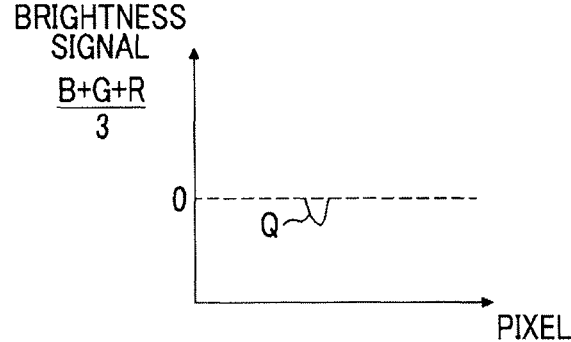

The brightness signal generation section 62b generates the brightness signal I (=(B+G+R)/3) by dividing the total value (B+G+R) of the signal values of the signals B, G, and R after gain adjustment by 3. Since the brightness signal I is obtained by averaging the signal values of the respective colors, the brightness signal I indicates the average brightness of the subject. As shown in FIG. 10A, the hypertrophy extraction section 62c extracts a pixel region, in which the pixel value is within a medium brightness range M of threshold values Th2 to Th3, of the brightness signal I as hypertrophy Q. As shown in FIG. 10B, in a hypertrophy image 80 in which the hypertrophy Q is extracted, the pixel value is used as it is for a pixel region where the pixel value is within the medium brightness range M, while the pixel value is set to "0" for a pixel region where the pixel value is not within the medium brightness range M.

Figure 11:
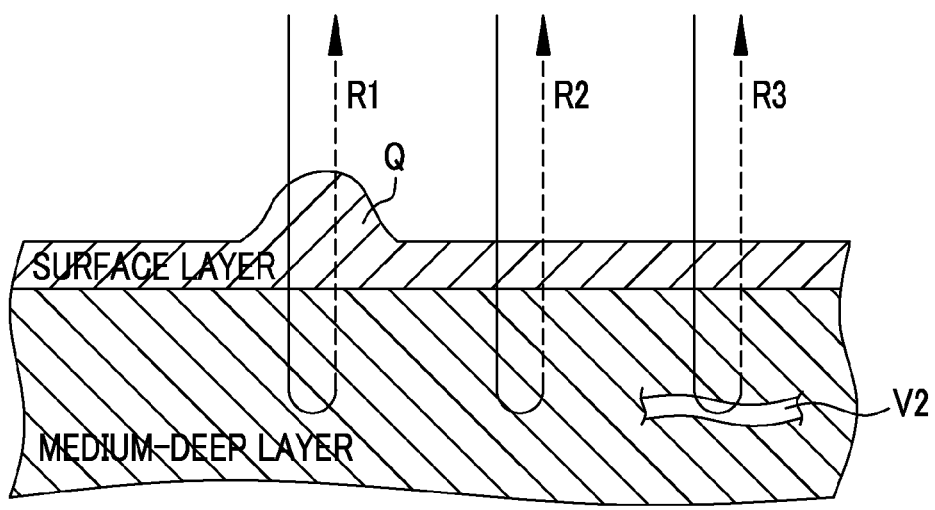
FIG. 11 is a diagram showing hypertrophy, a part that is not hypertrophy, and reflected light R1, R2, and R3 from the medium-deep layer blood vessel.

The reason why the pixel region where the pixel value is within the medium brightness range M is set as the hypertrophy Q is as follows. As shown in FIG. 11, in the hypertrophy Q, the thickness from the surface layer to the medium-deep layer is increased due to a ridge from the body tissue surface layer, compared with other parts that are not thickened. Accordingly, when emitting light having a wavelength exceeding 500 nm that has a degree of penetration to the medium-deep layer, the amount of reflected light R1 from the hypertrophy Q is reduced compared with the amount of reflected light R2 of other parts that are not thickened. On the other hand, the amount of reflected light R1 from the hypertrophy Q is not reduced compared with the amount of reflected light R3 when emitting light having a wavelength exceeding 500 nm to a medium-deep layer blood vessel V2. This is because the absorbance of the mucous membrane that forms the hypertrophy Q is lower than the absorbance of hemoglobin in the blood vessel. Therefore, a pixel region where the pixel value is within the medium brightness range M is set as the hypertrophy Q.

Figure 10C:
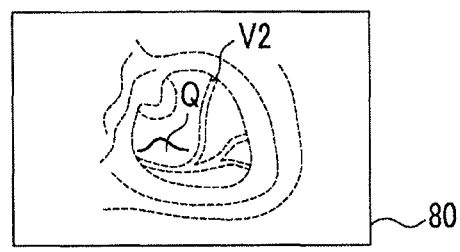

Then, low-frequency to medium-frequency filtering processing is performed on the hypertrophy image 80. A change in the brightness value of the hypertrophy portion is small compared with other parts. Therefore, as shown in FIG. 10C, the hypertrophy image 80 in which only the hypertrophy is sharply extracted is obtained by performing low-frequency to medium-frequency filtering.

Figure 12:
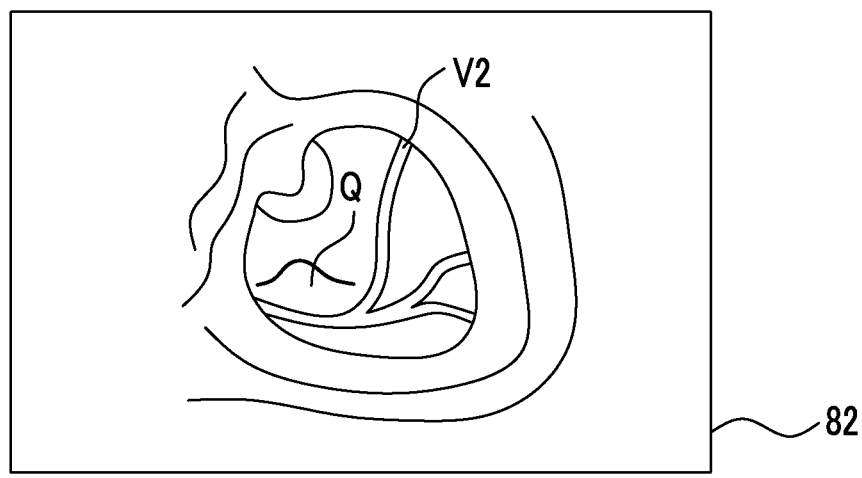
FIG. 12 is a diagram showing a hypertrophy enhancement image.

The image generation section 62d generates a hypertrophy enhancement image 82 shown in FIG. 12 by combining the normal light image with the hypertrophy image 80 obtained by the hypertrophy extraction section 62c. The generated hypertrophy enhancement image 82 is displayed on the monitor 14 by the display control circuit 58. Since the hypertrophy enhancement image 82 is based on the bright normal light image, it is possible to perform diagnosis while securing the visibility. In the hypertrophy enhancement image 82, only the hypertrophy Q of the biological information of the body tissue surface layer is clear. Accordingly, the hypertrophy enhancement image 82 is an image that is suitable when performing cancer diagnosis by focusing on only the hypertrophy.

As shown in FIG. 7, the irregularities and blood vessel enhancement image generation section 63 (a form of second composite image generation unit) includes a B/G image generation section 63a, a blood vessel extraction section 63b (a form of blood vessel extraction image generation unit), and an irregularities and blood vessel enhancement image generation section 63c. The B/G image generation section 63a generates a B/G image from the signal of the blue component and the signal of the green component among the signals acquired by the imaging of the image light of the white light. In each pixel of the B/G image, information of the brightness ratio B/G obtained by dividing the signal value of the blue signal B by the signal value of the green signal G is included. In the hypertrophy observation mode or the hypertrophy and blood vessel observation mode, the B/G image is generated from B and G On the other hand, in the superficial microstructure observation mode or the microstructure and blood vessel observation mode, the B/G image is generated from B1 and G1.

Figure 13:
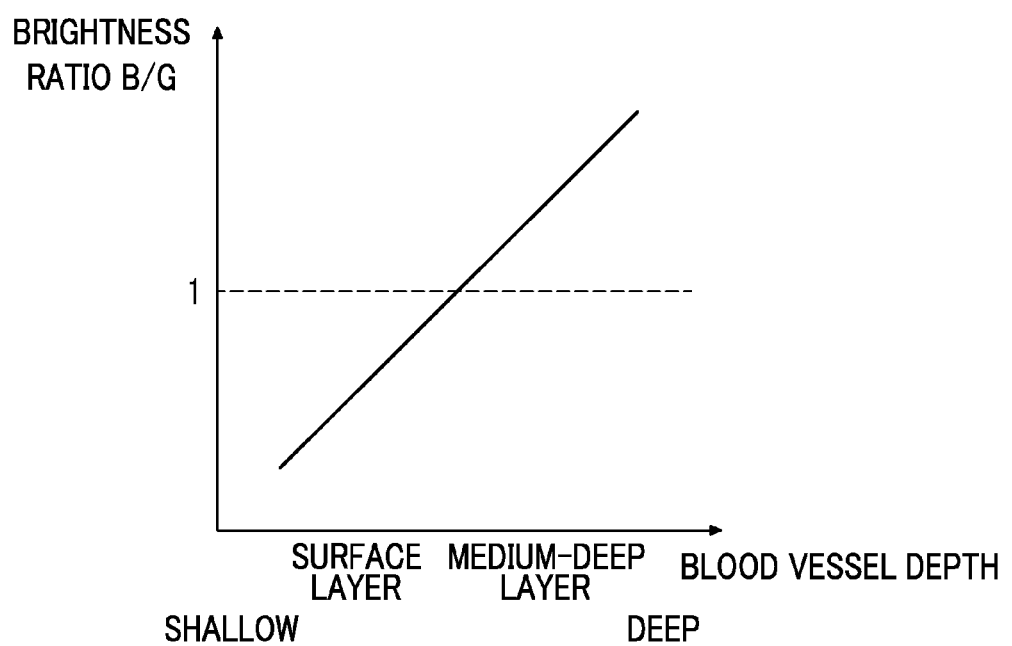
FIG. 13 is a graph showing the relationship between the brightness ratio B/G and the blood vessel depth.
Figure 14:
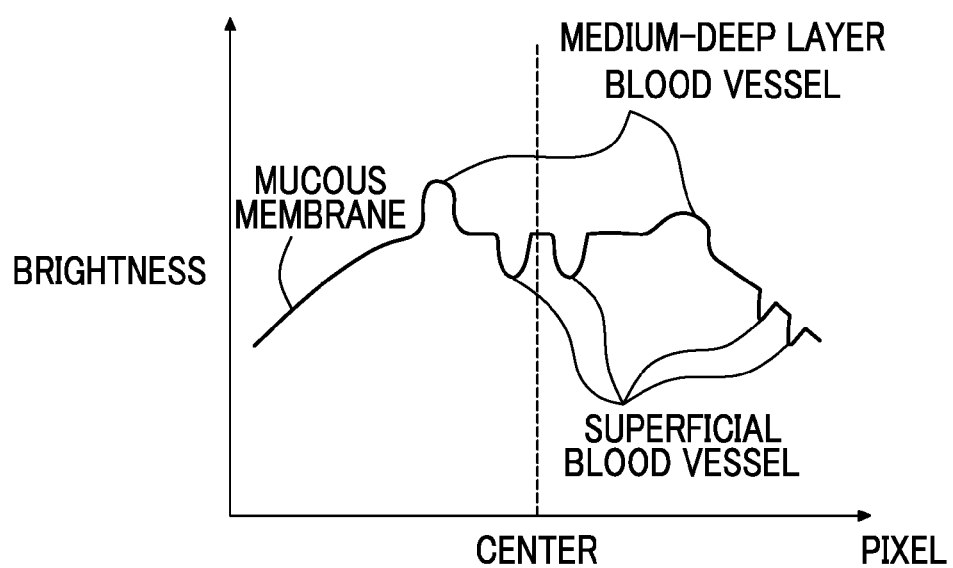
FIG. 14 is a graph showing the brightness distribution of a part of a B/G image.

The brightness ratio B/G of each pixel in the B/G image is relevant to the blood vessel depth. As shown in FIG. 13, there is a proportional relationship in which the brightness ratio B/G increases as the blood vessel depth increases. Accordingly, the magnitude relationship of "brightness of superficial blood vessel<brightness of mucous membrane<brightness of medium-deep layer blood vessel" is satisfied. In addition, as shown in the B/G image of FIG. 14, due to factors such as uneven brightness, there is a case where the brightness of the B/G image is the highest in the middle and decreases toward the periphery from the center. Therefore, the above-described magnitude relationship (brightness of superficial blood vessel<brightness of mucous membrane<brightness of medium-deep layer blood vessel) is locally satisfied, but may not be satisfied on the whole.

Figure 15:
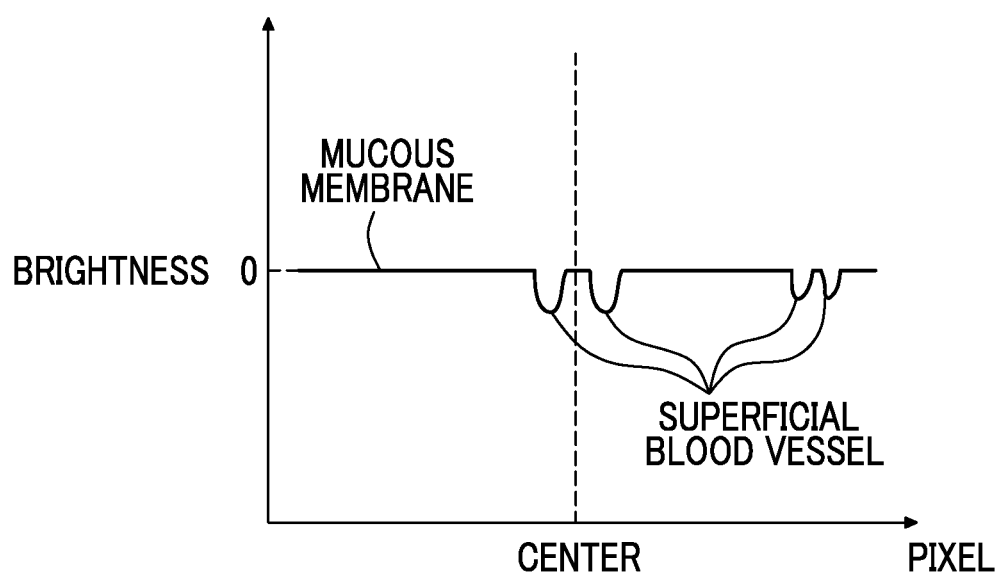
FIG. 15 is a graph showing the brightness distribution of a part of a superficial blood vessel extraction image.
Figure 16:
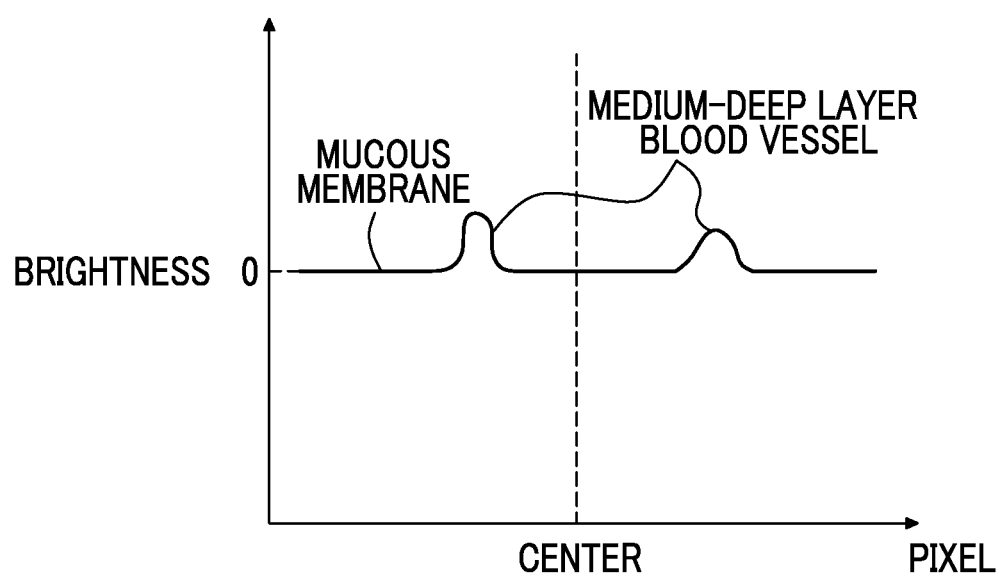
FIG. 16 is a graph showing the brightness distribution of a part of a medium-deep layer blood vessel image.

The blood vessel extraction section 63b generates a blood vessel extraction image by extracting a blood vessel located in a specific layer from the B/G image. The blood vessel extraction is performed by frequency filtering processing. When extracting a superficial blood vessel, high-frequency components, which are frequency band components, many of which are present in the superficial blood vessel, are extracted from the B/G image. As a result, as shown in FIG. 15, it is possible to obtain a superficial blood vessel extraction image in which the brightness of the superficial blood vessel is negative and the brightness of a mucous membrane portion is approximately "0". In the superficial blood vessel extraction image, only the superficial blood vessel is extracted sharply. On the other hand, when extracting a medium-deep layer blood vessel, medium-frequency components, which are frequency band components, many of which are present in the medium-deep layer blood vessel, are extracted from the B/G image. As a result, as shown in FIG. 16, it is possible to obtain a medium-deep layer blood vessel extraction image in which the brightness of the medium-deep layer blood vessel is positive and the brightness of a mucous membrane portion is approximately "0". In the medium-deep layer blood vessel extraction image, only the medium-deep layer blood vessel is extracted sharply.

Since the component of the mucous membrane becomes a value close to approximately "0" by performing the frequency filtering processing described above, it is possible to extract only a blood vessel portion. In addition, the above-described magnitude relationship (brightness of superficial blood vessel<brightness of mucous membrane<brightness of medium-deep layer blood vessel) is also satisfied on the whole.

Figure 17:
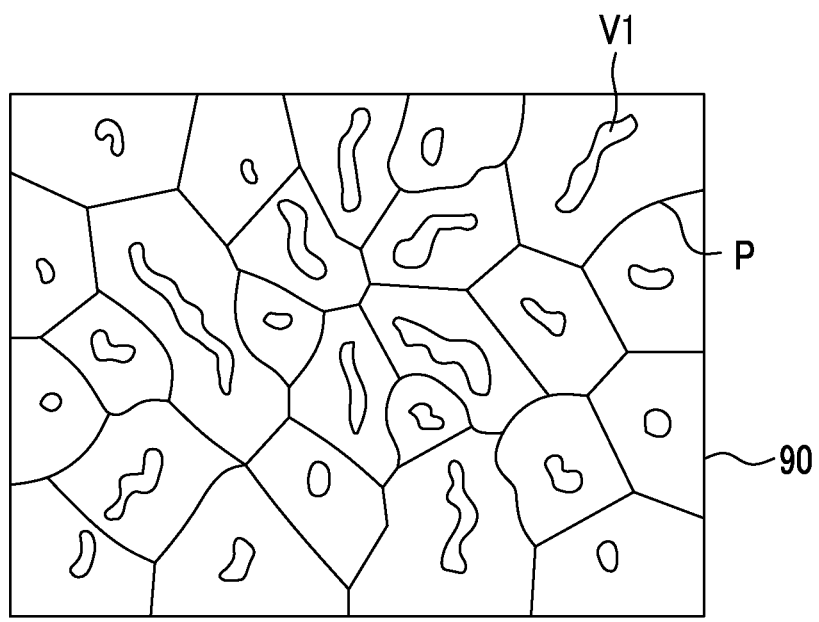
FIG. 17 is a diagram showing a microstructure and blood vessel enhancement image.

When the microstructure and blood vessel observation mode is set, the irregularities and blood vessel enhancement image generation section 65 generates a microstructure and blood vessel enhancement image, in which the superficial microstructure and the blood vessel of a specific layer are clear, by combining the superficial microstructure image, the blood vessel extraction image, and the normal light image. The generated microstructure and blood vessel enhancement image is displayed on the monitor 14 by the display control circuit 58. For example, when a superficial blood vessel extraction image is used as a blood vessel extraction image, a microstructure and blood vessel enhancement image 90 in which both a pit pattern P, which is configured to include a number of gland ducts, and a microvessel V1 between the gland ducts are clear is displayed, as shown in FIG. 17. Thus, by making clear both the pit pattern P and the microvessel V1, it is possible to improve the diagnostic performance in differentiating cancer.

Figure 18:
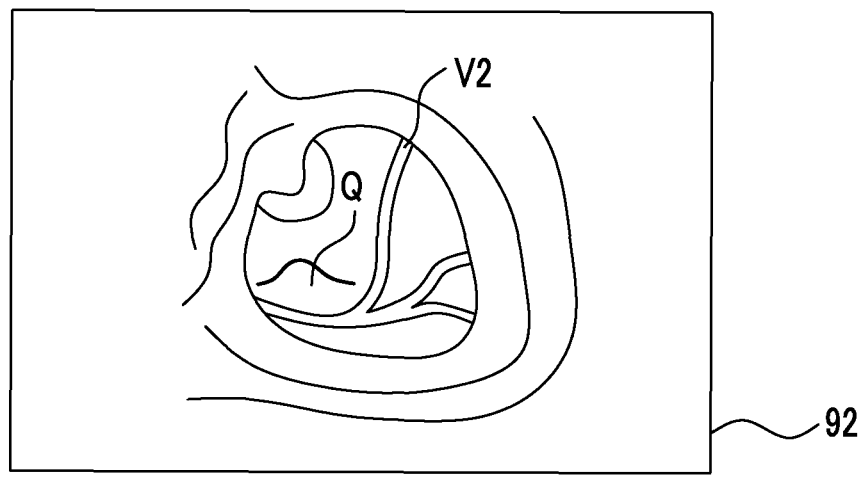
FIG. 18 is a diagram showing a hypertrophy and blood vessel enhancement image.

On the other hand, when the hypertrophy and blood vessel observation mode is set, the irregularities and blood vessel enhancement image generation section 65 generates a hypertrophy and blood vessel enhancement image, in which hypertrophy and the blood vessel of a specific layer are clear, by combining the hypertrophy image, the blood vessel extraction image, and the normal light image. The generated hypertrophy and blood vessel enhancement image is displayed on the monitor 14 by the display control circuit 58. For example, when a medium-deep layer blood vessel extraction image is used as a blood vessel extraction image, a hypertrophy and blood vessel enhancement image 92 in which both the hypertrophy Q and the medium-deep layer blood vessel V2 are clear is displayed, as shown in FIG. 18. Thus, by making clear both the medium-deep layer blood vessel V2 and the hypertrophy Q with a possibility of cancer, it becomes easy to detect a lesion at the time of screening.

Figure 19:
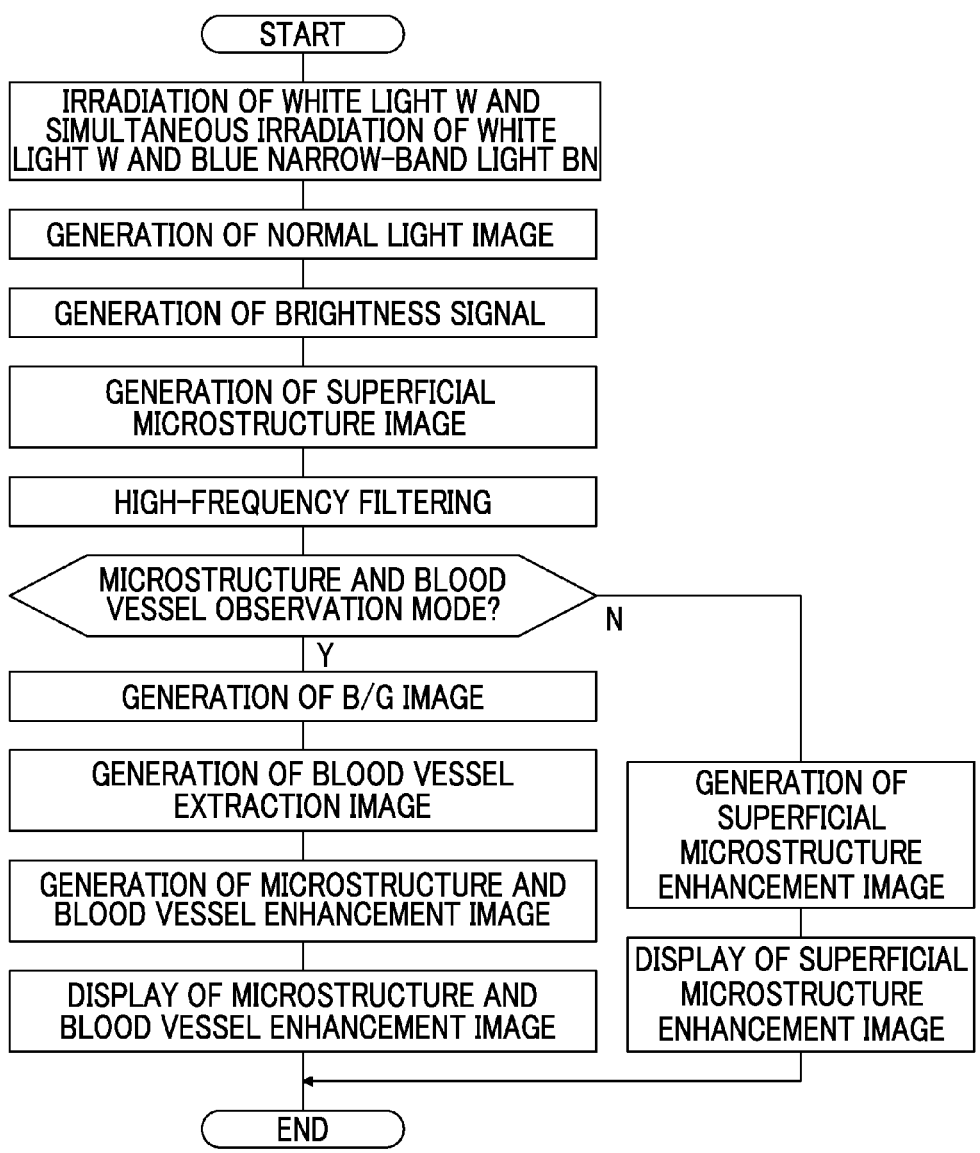
FIG. 19 is a flowchart showing a sequential flow in the superficial microstructure observation mode or the microstructure and blood vessel observation mode.

Next, a sequential flow in the superficial microstructure observation mode and the microstructure and blood vessel observation mode will be described with reference to the flowchart shown in FIG. 19.

When switching to the superficial microstructure observation mode or the microstructure and blood vessel observation mode is performed by the mode switch SW 15, the white light W is irradiated toward the subject. By imaging the subject illuminated with the white light W using the color CCD 44, the blue signal B1, the green signal G1, and the red signal R1 are output from the CCD 44. Then, the white light W and the blue narrow-band light BN are simultaneously irradiated toward the subject. By imaging the subject illuminated with the white light W and the blue narrow-band light BN using the CCD 44, the blue signal B2, the green signal G2, and the red signal R2 are output from the CCD 44.

Then, a normal light image is generated based on the blue signal B1, the green signal G1, and the red signal R1. Then, a brightness signal I is generated by dividing the total value (B2+G2+R2) of the signal values of the blue signal B2, G2, and R2 by 3. A superficial microstructure image is generated by extracting a pixel region exceeding the high-brightness threshold value Th1 of the brightness signal I. By performing high-frequency filtering on the generated superficial microstructure image 70, the superficial microstructure in the image is sharpened.

When the superficial microstructure observation mode is set, a superficial microstructure enhancement image is generated by combining the normal light image with the superficial microstructure image after frequency filtering. The generated superficial microstructure enhancement image is displayed on the monitor 14. The series of operations described above are repeatedly performed while the superficial microstructure observation mode is set.

On the other hand, when the microstructure and blood vessel observation mode is set, a B/G image having a brightness ratio B/G between the blue signal B1 and the green signal G1 is generated. After the B/G image is generated, a blood vessel of a specific layer is extracted from the B/G image. As a result, a blood vessel extraction image is obtained. A microstructure and blood vessel enhancement image is generated by combining the blood vessel extraction image, the superficial microstructure enhancement image 70, and the normal light image. The generated microstructure and blood vessel enhancement image is displayed on the monitor 14. The series of operations described above are repeatedly performed while the microstructure and blood vessel observation mode is set.

Figure 20:
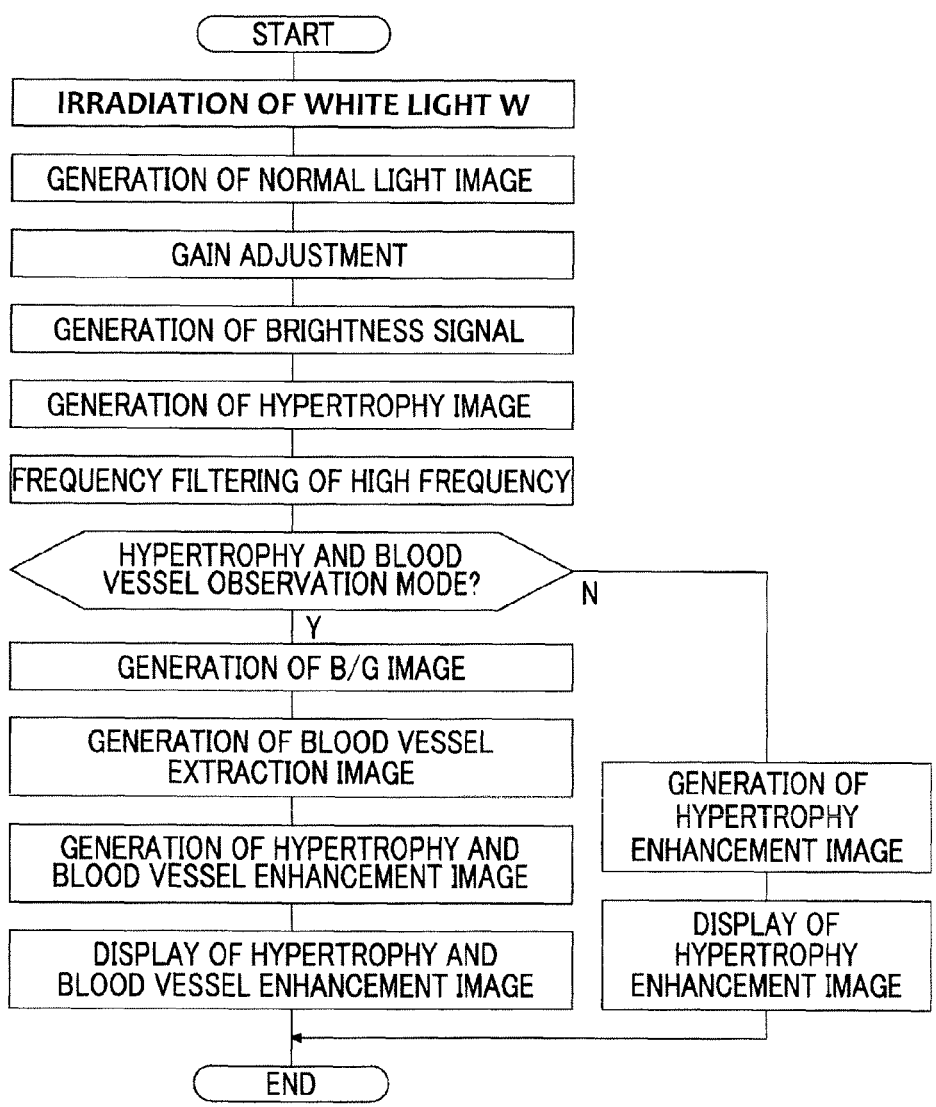
FIG. 20 is a flowchart showing a sequential flow in the hypertrophy observation mode or the hypertrophy and blood vessel observation mode.

Next, a sequential flow in the hypertrophy observation mode and the hypertrophy and blood vessel observation mode will be described with reference to the flowchart shown in FIG. 20.

When switching to the hypertrophy observation mode or the hypertrophy and blood vessel observation mode is performed by the mode switch SW 15, the white light W is irradiated toward the subject. By imaging the subject illuminated with the white light W using the color CCD 44, the blue signal B, the green signal G, and the red signal R are output from the CCD 44.

Then, a normal light image is generated based on the blue signal B, the green signal G, and the red signal R. In addition, the gain of the signals B, G, and R is adjusted to reduce the pixel value of the signal B and increase the pixel values of the signals G and R. Then, the brightness signal I is generated by dividing the total value (B+G+R) of the signal values of the signals B, G, and R after gain adjustment by 3. A hypertrophy image is generated by extracting a pixel region less than the low-brightness threshold value Th2 of the brightness signal I. By performing low-frequency to medium-frequency filtering on the generated hypertrophy image, the hypertrophy in the image is sharpened.

When the hypertrophy observation mode is set, a hypertrophy enhancement image is generated by combining the normal light image with the hypertrophy image after frequency filtering. The generated hypertrophy enhancement image is displayed on the monitor 14. The series of operations described above are repeatedly performed while the hypertrophy observation mode is set.

On the other hand, when the hypertrophy and blood vessel observation mode is set, a B/G image having a brightness ratio B/G between the blue signal B and the green signal G is generated. After the B/G image is generated, a blood vessel of a specific layer is extracted from the B/G image. As a result, a blood vessel extraction image is obtained. A hypertrophy and blood vessel enhancement image is generated by combining the blood vessel extraction image, the hypertrophy enhancement image, and the normal light image. The generated hypertrophy and blood vessel enhancement image is displayed on the monitor 14. The series of operations described above are repeatedly performed while the hypertrophy and blood vessel observation mode is set.

Figure 21:
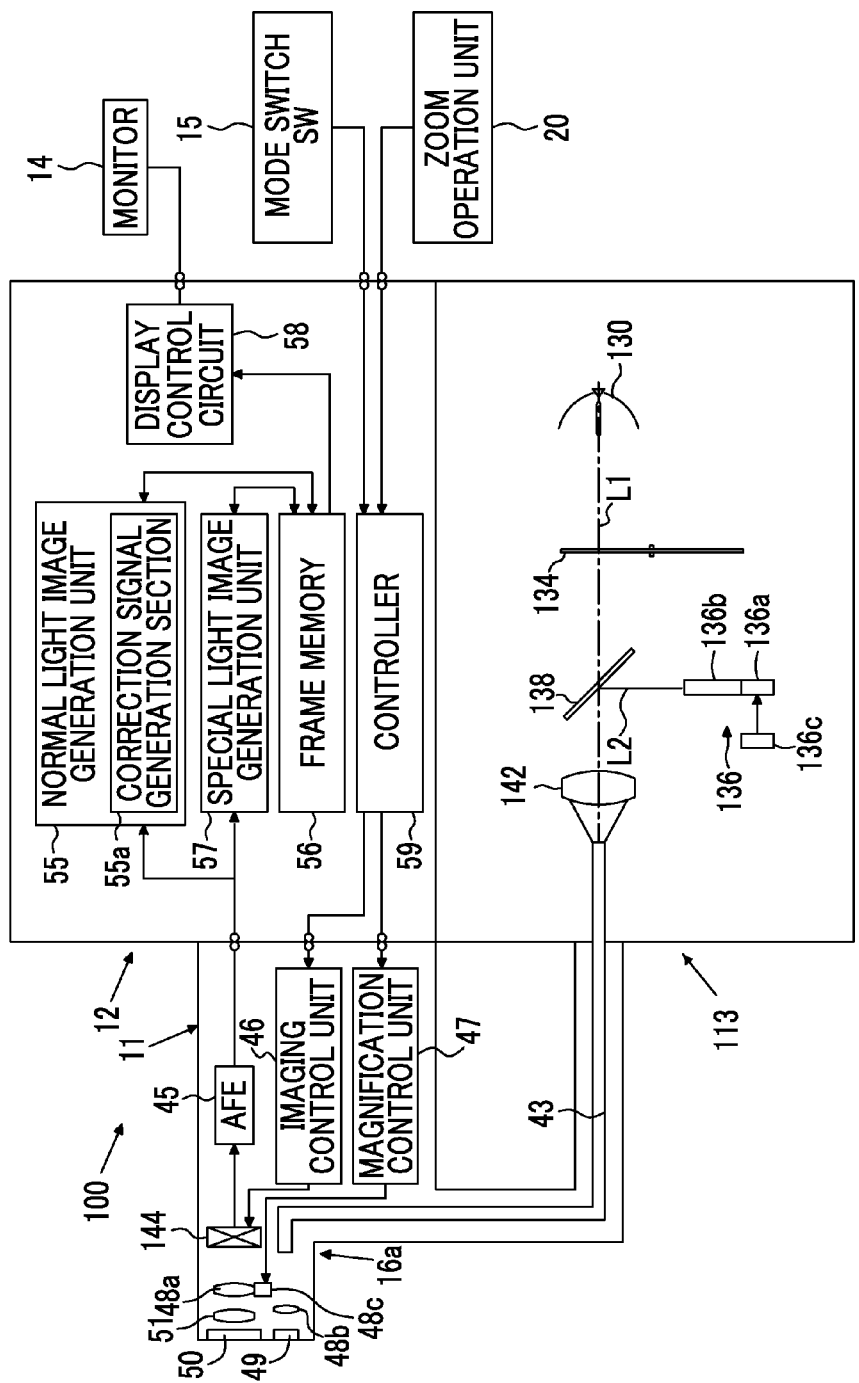
FIG. 21 is a diagram showing the internal configuration of an endoscope system of a second embodiment.

In a second embodiment of the present invention, unlike the first embodiment of the simultaneous system using the color CCD, subject imaging is performed in a frame sequential method using the rotary filter of RGB. As shown in FIG. 21, in an endoscope system 100 of the second embodiment, the configuration of a light source device 113 is different from that of the light source device 13 of the first embodiment. In addition, the phosphor 40 is not provided in the distal portion 16*a* of the electronic endoscope 11. In addition, the configuration of the CCD and the operation of the imaging control unit 46 in the electronic endoscope 11 are different from those in the first embodiment. In addition, the method of generating a normal light image in the microstructure observation mode and the microstructure and blood vessel observation mode is different. Since others are the same as those described in the first embodiment, only the differences from the first embodiment will be described below.

The light source device 113 includes: a white light source 130 that emits broadband light BB (400 nm to 700 nm); a rotary filter 134 that separates the broadband light BB from the white light source 130 into light beams of three colors of B, G, and R and sequentially supplies these light beams of respective colors to the light guide 43; a semiconductor light source unit 136 that emits the blue narrow-band light BN; and a light joining unit 138 that makes the blue narrow-band light BN join the optical path L1 of the broadband light BB between the rotary filter 134 and the light guide 43.

Figure 22:
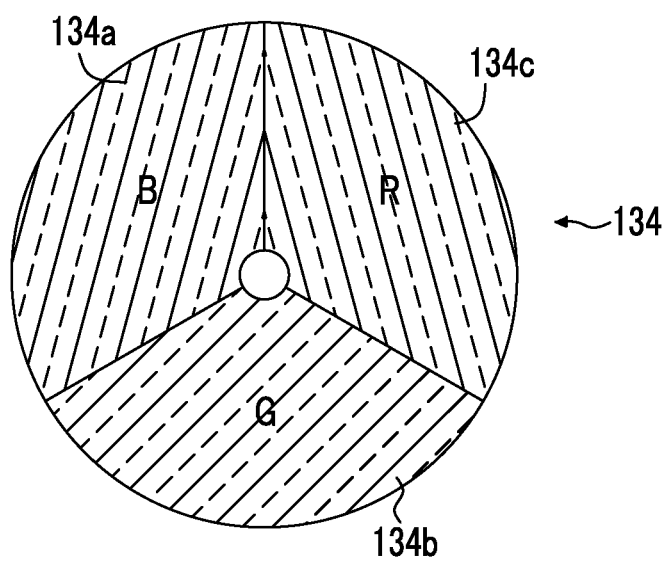
FIG. 22 is a diagram showing a rotary filer.

The white light source 130 is formed of a xenon lamp, a halogen lamp, a metal halide, or the like. As shown in FIG. 22, the rotary filter 134 is rotatably provided so that a B filter portion 134*a*, a G filter portion 134*b*, and an R filter portion 134*c* are selectively inserted in the optical path L1 of the broadband light BB. The rotary filter 134 has a disc shape, and is divided into three regions, each of which is a fan-shaped region having a central angle of 120°, in the circumferential direction, and the B filter portion 134*a*, the G filter portion 134*b*, and the R filter portion 134*c* are respectively provided in the three regions.

Figure 23:
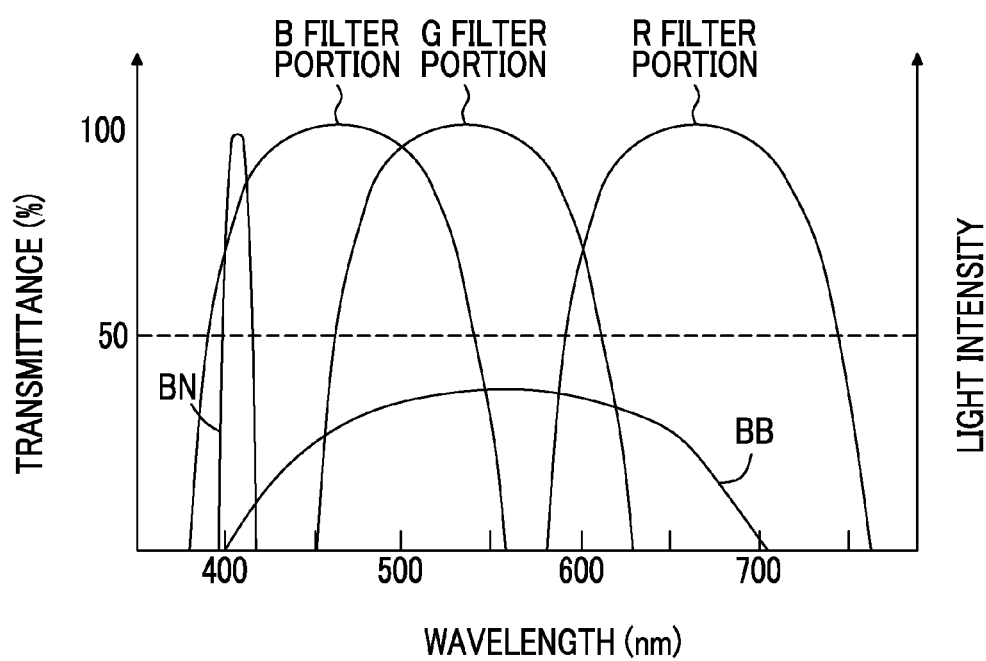
FIG. 23 is a graph showing the spectral transmittances of a B filter, a G filter, and an R filter and the emission intensities of broadband light BB and blue narrow-band light RN.

As shown in FIG. 23, the B filter portion 134*a* allows B light of the blue band from the broadband light BB to be transmitted therethrough, the G filter portion 134*b* allows G light of the green band from the broadband light BB to be transmitted therethrough, and the R filter portion 134*c* allows R light of the red band from the broadband light BB to be transmitted therethrough. Therefore, B light, G light, and R light are sequentially emitted from the rotary filter 134 by the rotation of the rotary filter 134.

The semiconductor light source unit 136 includes a blue narrow-band light source 136*a*, an optical fiber 136*b*, and a light source control section 136*c*. As shown in FIG. 23, the blue narrow-band light source 136*a* is a semiconductor light source, such as a laser diode, and emits the blue narrow band BN having a center wavelength of 405 nm. The blue narrow-band light source 136*a* is turned on and off according to the control of the light source control section 136*c*. In the normal observation mode, the hypertrophy observation mode, and the hypertrophy and blood vessel observation mode, the blue narrow-band light source 236*a* is always in the OFF state. In the microstructure observation mode and the microstructure and blood vessel observation mode, only the blue narrow-band light source 136*a* is turned on only when the B filter 134*a* of the rotary filter 134 is inserted in the optical path L1 of the broadband light BB, and the blue narrow-band light source 136*a* is turned off when the other G and R filters 134*b* and 134*c* are inserted in the optical path L1.

The blue narrow-band light BN from the blue narrow-band light source 136*a* is incident on the optical fiber 136*b*. The blue narrow-band light BN is emitted toward the light joining unit 138 through a collimator lens (not shown). The light joining unit 138 is a dichroic mirror. Light from the rotary filter 134 is transmitted through the light joining unit 138 as it is, while the blue narrow-band light BN from the semiconductor light source unit 136 is reflected from the light joining unit 138. Accordingly, the optical path L2 of the blue narrow-band light BN is made to match the optical path L1 of the broadband light BB. Light emitted from the light joining unit 138 is incident on the light guide 43 through a condensing lens 142.

A CCD 144 in the electronic endoscope is a monochrome imaging device in which a micro color filter is not provided on the imaging surface, unlike in the first embodiment described above. The imaging control unit 46 that controls the imaging of the CCD 144 also performs a different operation from that in the first embodiment described above.

Figure 24A:
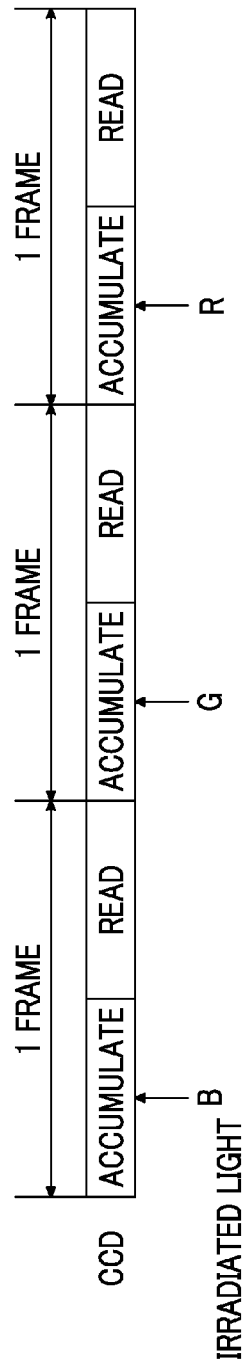
FIG. 24A is a diagram for explaining the imaging control of a CCD in a normal observation mode, a hypertrophy observation mode, and a hypertrophy and blood vessel observation mode in the second embodiment.

In the normal observation mode, the hypertrophy observation mode, and the hypertrophy and blood vessel observation mode, as shown in FIG. 24A, image light beams of three colors of B, G, and R are sequentially captured and the electric charges are accumulated, and frame sequential imaging signals B, G, and R are sequentially output based on the accumulated electric charges. The series of operations are repeated while the normal observation mode, the hypertrophy observation mode, and the hypertrophy and blood vessel observation mode are set. The frame sequential imaging signals B, G, and R correspond to B, G, and R of the first embodiment, respectively.

Figure 24B:
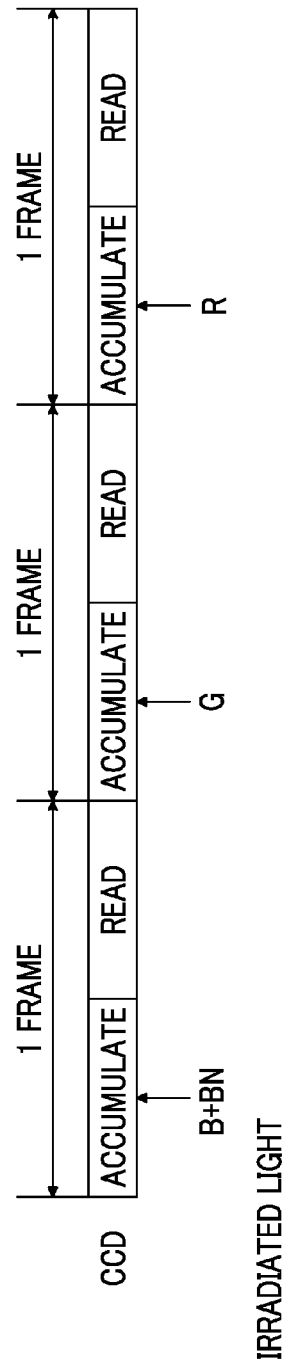
FIG. 24B is a diagram for explaining the imaging control of the CCD in a superficial microstructure observation mode and a microstructure and blood vessel observation mode in the second embodiment.

In the microstructure observation mode and the microstructure and blood vessel observation mode, as shown in FIG. 24B, image light of mixed color light of the light of B color and the blue narrow-band light BN that are simultaneously irradiated, image light of the light of G color, and image light of the light of R color are sequentially captured and the electric charges are accumulated, and frame sequential imaging signals B+BN, G, and R are sequentially output based on the accumulated electric charges. The series of operations are repeated while the surface layer observation mode is set. The frame sequential imaging signals B+BN, G, and R correspond to B2, G2, and R2 of the first embodiment, respectively.

In the second embodiment, when generating a normal light image in the microstructure observation mode and the microstructure and blood vessel observation mode, a correction signal generation section 55a in the normal light image generation unit 55 generates a correction signal B' by removing the component of the blue narrow-band light BN from the frame sequential imaging signal B+BN, and generates a normal light image using the correction signal B' and the frame sequential imaging signals G and R. The correction signal generation section 55a generates the correction signal B' by multiplying the frame sequential imaging signal B+BN by a correction coefficient k that is determined in advance from the relationship between the amount of light of B color and the amount of blue narrow-band light BN or the like.

In the first and second embodiments described above, a pixel region where the pixel value exceeds the threshold value Th1 of the brightness signal I is set as the superficial microstructure. Instead of this, however, a pixel region where the pixel value is within the high brightness range N of the threshold values Th4 to Th5 of the high brightness signal I may be set as the superficial microstructure. The upper limit Th5 of the high brightness range N is set to be lower than the brightness value of halation caused by specular reflection of illumination light. Therefore, it is possible to extract only the superficial microstructure instead of a halation region by performing extraction processing based on the high brightness range N. In addition, the threshold value Th1 is included in the high brightness range N.

What is claimed is:

1. An endoscope system, comprising:
an imaging device that acquires an image signal by imaging a subject; and
a processor device performs to,
generate a normal light image, in which a wavelength component of a visible light region is included, based on the image signal,
generate an irregularity image by extracting only information of irregularities on the subject from the image signal,
generate a first composite image by combining the normal light image with the irregularity image,
generate a blood vessel extraction image by extracting an image of a blood vessel located at a specific depth in the subject based on the image signal,
generate a second composite image by combining the normal light image, the blood vessel extraction image, and the irregularity image;
wherein the image signal is configured to include image signals of a plurality of colors including at least a blue signal, which has a blue light component having a degree of penetration to a surface layer of body tissue of the subject, and a green signal, which has a green light component having a degree of penetration to a medium-deep layer of the body tissue, and
the processor device extracts the image of blood vessel at the specific depth based on a ratio of the blue signal and the green signal of the image signals of the plurality of colors.

2. The endoscope system according to claim 1,
wherein the processor device further performs to generate a microstructure image as the irregularity image by extracting only a microstructure of a body tissue surface layer from the image signal, and
the processor device further performs to generate a first composite image by combining the normal light image with the microstructure image.

3. The endoscope system according to claim 2,
wherein the processor device further performs frequency filtering of a frequency corresponding to a depth of a blood vessel on the blood vessel extraction image.

4. The endoscope system according to claim 2,
wherein imaging of the subject is performed by a color imaging device having pixels of a plurality of colors in which respective color separation filters are provided.

5. The endoscope system according to claim 2, further comprising:
a light source that sequentially irradiates the subject with light beams of a plurality of colors,
wherein imaging of the subject is performed by a monochrome imaging device whenever sequential irradiation is performed by the illumination unit.

6. The endoscope system according to claim 2, further comprising:
a display unit that displays the irregularity image.

7. The endoscope system according to claim 1,
wherein the processor device further performs to generate a hypertrophy image as the irregularity image by extracting from the image signal only hypertrophy having a thickness from a body tissue surface layer to a medium-deep layer, and
the processor device further performs to generate a first composite image by combining the normal light image with the hypertrophy image.

8. The endoscope system according to claim 7,
wherein the processor device further performs frequency filtering of a frequency corresponding to a depth of a blood vessel on the blood vessel extraction image.

9. The endoscope system according to claim 7,
wherein imaging of the subject is performed by a color imaging device having pixels of a plurality of colors in which respective color separation filters are provided.

10. The endoscope system according to claim 7, further comprising:
a light source that sequentially irradiates the subject with light beams of a plurality of colors,
wherein imaging of the subject is performed by a monochrome imaging device whenever sequential irradiation is performed by the illumination unit.

11. The endoscope system according to claim 7, further comprising:
   a display unit that displays the irregularity image.

12. The endoscope system according to claim 1,
   wherein the processor device further performs frequency filtering of a frequency corresponding to a depth of a blood vessel on the blood vessel extraction image.

13. The endoscope system according to claim 12,
   wherein imaging of the subject is performed by a color imaging device having pixels of a plurality of colors in which respective color separation filters are provided.

14. The endoscope system according to claim 12, further comprising:
   a light source that sequentially irradiates the subject with light beams of a plurality of colors,
   wherein imaging of the subject is performed by a monochrome imaging device whenever sequential irradiation is performed by the illumination unit.

15. The endoscope system according to claim 12, further comprising:
   a display unit that displays the irregularity image.

16. The endoscope system according to claim 1,
   wherein imaging of the subject is performed by a color imaging device having pixels of a plurality of colors in which respective color separation filters are provided.

17. The endoscope system according to claim 1, further comprising:
   a light source that sequentially irradiates the subject with light beams of a plurality of colors,
   wherein imaging of the subject is performed by a monochrome imaging device whenever sequential irradiation is performed by the illumination unit.

18. The endoscope system according to claim 1, further comprising:
   a display unit that displays the irregularity image.

19. An image generation method, comprising:
   acquiring an image signal by imaging a subject with an imaging device;
   generating a normal light image, in which a wavelength component of a visible light region is included, based on the image signal using a processor device;
   generating an irregularity image by extracting only information of irregularities on the subject from the image signal using the processor device;
   generating a first composite image by combining the normal light image with the irregularity image using the processor device;
   generating blood vessel extraction image by extracting a blood vessel located at a specific depth in the subject based on the image signal;
   generating a second composite image by combining the normal light image, the blood vessel extraction image, and the irregularity image;
   wherein the image signal is configured to include image signals of a plurality of colors including at least a blue signal, which has a blue light component having a degree of penetration to a surface layer of body tissue of the subject, and a green signal, which has a green light component having a degree of penetration to a medium-deep layer of the body tissue; and
   generating an image of the blood vessel at the specific depth based on a ratio of the blue signal and the green signal of the image signals of the plurality of colors.

* * * * *